United States Patent [19]

Bundy

[11] 4,148,827

[45] Apr. 10, 1979

[54] 2-DECARBOXY-2-ALKYLCARBONYL PGD COMPOUNDS

[75] Inventor: Gordon L. Bundy, Portage, Mich.

[73] Assignee: The Upjohn Company, Kalamzoo, Mich.

[21] Appl. No.: 925,256

[22] Filed: Jul. 17, 1978

Related U.S. Application Data

[62] Division of Ser. No. 888,695, Mar. 21, 1978, Pat. No. 4,123,463.

[51] Int. Cl.$^2$ ........................................... C07C 177/00
[52] U.S. Cl. .................................................. 260/590 C
[58] Field of Search .................................... 260/590 C

[56] References Cited

U.S. PATENT DOCUMENTS

| | | | |
|---|---|---|---|
| 3,931,296 | 1/1976 | Hayashi et al. | 560/121 |
| 3,953,435 | 4/1976 | Hayashi et al. | 542/426 |
| 4,066,751 | 1/1978 | Hayashi et al. | 560/121 |

OTHER PUBLICATIONS

Derwent CPI Farmdoc 93049X/50 (JA-044211).
Derwent Farmdoc CPI No. 35953X.
Derwent Farmdoc CPI No. 94924X.

*Primary Examiner*—Gerald A. Schwartz
*Attorney, Agent, or Firm*—Robert A. Armitage

[57] ABSTRACT

The present invention provides novel prostaglandin analogs wherein the C-2 carboxyl is replaced by alkylcarbonyl, i.e., a C-2 ketone. These novel 2-decarboxy-2-alkylcarbonyl-PG-type compounds are disclosed as improved gastrointestinal cytoprotective agents, being devoid or substantially devoid of other prostaglandin-type effects (e.g., smooth muscle or cardiovascular).

33 Claims, No Drawings

2-DECARBOXY-2-ALKYLCARBONYL PGD COMPOUNDS

The present application is a divisional application of Ser. No. 888,695, filed Mar. 21, 1978, now U.S. Pat. No. 4,123,463.

The present invention relates to prostaglandin analogs, for which the essential material constituting disclosure therefor is incorporated by reference here from U.S. Pat. No. 4,123,463.

I claim:

1. A prostaglandin analog of the formula

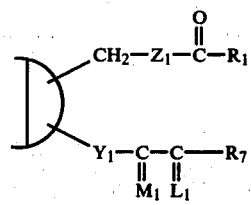

wherein ⊃ is

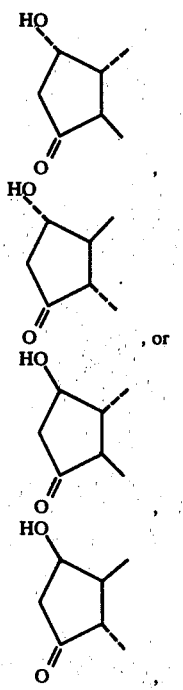

wherein $R_1$ is alkyl of one to 4 carbon atoms, inclusive; wherein $L_1$ is

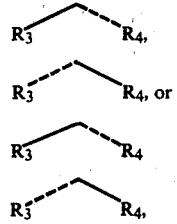

wherein $R_3$ and $R_4$ are hydrogen, methyl, or fluoro, being the same or different, with the proviso that one of $R_3$ and $R_4$ is methyl only when the other is hydrogen or methyl;

wherein $M_1$ is

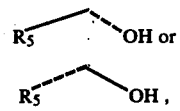

wherein $R_5$ is hydrogen or methyl;
wherein $R_7$ is $-(CH_2)_m-CH_3$,  (1)

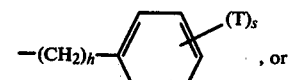, or  (2)

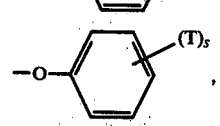  (3)

wherein h is zero to three, inclusive, wherein m is one to 5, inclusive, s is zero, one, 2, or 3 and T is chloro, fluoro, trifluoromethyl, alkyl of one to 3 carbon atoms or alkoxy of one to 3 carbon atoms, the various T's being the same or different, with the proviso that not more than two T's are other than alkyl;

wherein $Y_1$ is
(1) trans—CH=CH—,
(2) cis—CH=CH—,
(3) —CH$_2$CH$_2$—, or
(4) —C≡C—; and wherein $Z_1$ is

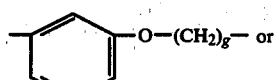  (1)

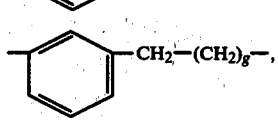,  (2)

wherein g is one, two, or three.

2. A prostaglandin analog according to claim 1, wherein $R_1$ is methyl.

3. A prostaglandin analog according to claim 2, wherein ⊃ is

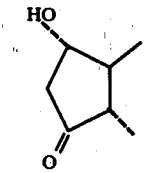

4. 2-Decarboxy-2-methylcarbonyl-8β,12α-PGD$_2$, a prostaglandin analog according to claim 3.

5. A prostaglandin analog according to claim 2, wherein ⊃ is

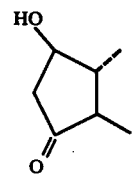

6. 2-Decarboxy-2-methylcarbonyl-9β, PGD₂, a prostaglandin analog according to claim 5.

7. A prostaglandin analog according to claim 2, wherein Ɖ is

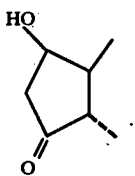

8. 2-Decarboxy-2-methylcarbonyl-8β, 9β, 12α-PGD₂, a prostaglandin analog according to claim 7.

9. A prostaglandin analog according to claim 2, wherein Ɖ is

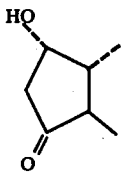

10. A prostaglandin analog according to claim 9, wherein $Y_1$ is cis—CH=CH—.

11. 2-Decarboxy-2-methylcarbonyl-3,7-inter-m-phenylene-3-oxo-4,5,6-trinor13-cis-PGD₂, a prostaglandin analog according to claim 10.

12. A prostaglandin analog according to claim 9, wherein $Y_1$ is —CH₂CH₂—.

13. 2-Decarboxy-2-methylcarbonyl-3,7-inter-m-phenylene-3-oxa-4,5,6-trinor13,14-dihydro-PGD₂, a prostaglandin analog according to claim 12.

14. A prostaglandin analog according to claim 9, wherein $Y_1$ is —C≡C—.

15. 2-Decarboxy-2-methylcarbonyl-3,7-inter-m-phenylene-3-oxa-4,5,6-trinor13,14-didehydro-PGD₂, a prostaglandin analog according to claim 14.

16. A prostaglandin analog according to claim 9, wherein $Y_1$ is trans—CH=CH—.

17. A prostaglandin analog according to claim 16, wherein $R_7$ is

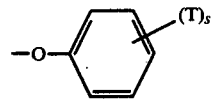

18. 2-Decarboxy-2-methylcarbonyl-3,7-inter-m-phenylene-3-oxa-4,5,6,18,19,20hexanor-17-phenyl-PGD₂, a prostaglandin analog according to claim 17.

19. A prostaglandin analog according to claim 16, wherein $R_7$ is

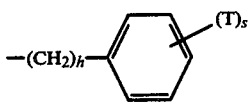

20. 2-Decarboxy-2-methylcarbonyl-3,7-inter-m-phenylene-3-oxa-4,5,6,17,18,-19,20-heptanor-16-phenoxy-PGD₂, a prostaglandin analog according to claim 19.

21. A prostaglandin analog according to claim 16, wherein $R_7$ is —(CH₂)$_m$—CH₃—.

22. A prostaglandin analog according to claim 21, wherein $Z_1$ is

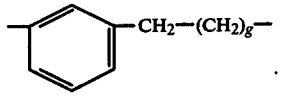

23. 2-Decarboxy-2-methylcarbonyl-3,7-inter-m-phenylene-4,5,6-trinorPGD₂, a prostaglandin analog according to claim 22.

24. A prostaglandin analog according to claim 21, wherein $Z_1$ is

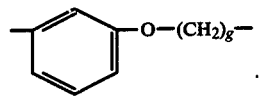

25. A prostaglandin analog according to claim 21, wherein $R_5$ is methyl.

26. 2-Decarboxy-2-methylcarbonyl-3,7-inter-m-phenylene-3-oxo-4,5,6-trinor-15-methyl-PGD₂, a prostaglandin analog according to claim 21.

27. A prostaglandin analog according to claim 21, wherein $R_5$ is hydrogen.

28. A prostaglandin analog according to claim 27, wherein one of $R_3$ and $R_4$ is fluoro.

29. 2-Decarboxy-2-methylcarbonyl-3,7-inter-m-phenylene-3-oxa-4,5,6-trinor-16,16-difluoro-PGD₂, a prostaglandin analog according to claim 28.

30. A prostaglandin analog according to claim 27, wherein at least one of $R_3$ and $R_4$ is methyl.

31. 2-Decarboxy-2-methylcarbonyl-3,7-inter-m-phenylene-3-oxa-4,5,6-trinor16,16-dimethyl-PGD₂, a prostaglandin analog according to claim 30.

32. A prostaglandin analog according to claim 27, wherein $R_3$ and $R_4$ are both hydrogen.

33. 2-Decarboxy-2-methylcarbonyl-3,7-inter-m-phenylene-3-oxo-4,5,6-trinorPGD₂, a prostaglandin analog according to claim 32.

* * * * *

UNITED STATES PATENT AND TRADEMARK OFFICE
CERTIFICATE OF CORRECTION

PATENT NO. : 4,148,827
DATED : April 10, 1979
INVENTOR(S) : Gordon L. Bundy

It is certified that error appears in the above-identified patent and that said Letters Patent are hereby corrected as shown below:

Column 2, line 31, "-C=C-;" should read -- -C≡C-; --;

Column 3, line 39, "-C=C-." should read -- -C≡C-. --.

Signed and Sealed this

Thirty-first Day of July 1979

[SEAL]

Attest:

*Attesting Officer*

LUTRELLE F. PARKER
*Acting Commissioner of Patents and Trademarks*

UNITED STATES PATENT OFFICE
CERTIFICATE OF CORRECTION

Patent No. 4,148,827  Dated April 10, 1979

Inventor(s) Gordon L. Bundy

It is certified that error appears in the above-identified patent and that said Letters Patent are hereby corrected as shown below:

Column 2, line 57, "2-methylcarbonyl-8β,12α-$PGD_2$," should read -- 2-methylcarbonyl-3,7-inter-m-phenylene-3-oxa-4,5,6-trinor-8β,12α-$PGD_1$, --;

Column 3, line 1, "2-methylcarbonyl-9β-$PGD_2$," should read -- 2-methylcarbonyl-3,7-inter-m-phenylene-3-oxa-4,5,6-trinor-9β-$PGD_1$, --; lines 14-15, "2-methylcarbonyl-8β,9β,12α-$PGD_2$," should read -- 2-methylcarbonyl-3,7-inter-m-phenylene-3-oxa-4,5,6-trinor-8β,9β,12α-$PGD_1$, --; line 30, "3-oxo-4,5,6-trinor13-cis-$PGD_2$," should read -- 3-oxa-4,5,6-trinor-13-cis-$PGD_1$, --; lines 36, 41, 55, "$PGD_2$," should read -- $PGD_1$, --;

Column 4, line 11, 23, 43, and 48, "$PGD_2$," should read -- $PGD_1$, --; line 36, "3-oxo-4,5,6-trinor-15-methyl-$PGD_2$," should read -- 3-oxa-4,5,6-trinor-15-methyl-$PGD_1$, --; line 54, "3-oxo-4,5,6-trinor$PGD_2$," should read -- 3-oxa-4,5,6-trinor-$PGD_1$, --.

Signed and Sealed this

Sixth Day of November 1979

[SEAL]

Attest:

RUTH C. MASON
Attesting Officer

LUTRELLE F. PARKER
Acting Commissioner of Patents and Trademarks